United States Patent
Roehm, III et al.

(10) Patent No.: US 7,618,431 B2
(45) Date of Patent: Nov. 17, 2009

(54) OVAL DILATOR AND RETRACTOR SET AND METHOD

(75) Inventors: Thomas E. Roehm, III, Braden, TN (US); William B. Null, Olive Branch, MS (US)

(73) Assignee: Warsaw Orthopedic, Inc.

( * ) Notice: Subject to any disclaimer, the term of this patent is extended or adjusted under 35 U.S.C. 154(b) by 197 days.

(21) Appl. No.: 11/478,041

(22) Filed: Jun. 29, 2006

(65) Prior Publication Data

US 2006/0247651 A1     Nov. 2, 2006

Related U.S. Application Data

(62) Division of application No. 10/246,995, filed on Sep. 19, 2002, now Pat. No. 7,074,226.

(51) Int. Cl.
*A61M 29/00* (2006.01)
*A61B 17/58* (2006.01)

(52) U.S. Cl. .......................... 606/191; 606/90; 600/210

(58) Field of Classification Search ................ 606/191, 606/193, 194, 197, 198, 199, 90, 105, 99; 604/164.05, 161; 600/210
See application file for complete search history.

(56) References Cited

U.S. PATENT DOCUMENTS

| | | | |
|---|---|---|---|
| 672,377 A | 4/1901 | Kearns | |
| 1,719,428 A * | 7/1929 | Friedman | .................... 604/105 |
| 4,545,374 A | 10/1985 | Jacobson | |
| RE32,158 E * | 5/1986 | Vukovic | ...................... 600/123 |
| 5,176,128 A | 1/1993 | Andrese | |
| 5,269,772 A | 12/1993 | Wilk | |
| 5,472,426 A * | 12/1995 | Bonati et al. | ............. 604/164.1 |
| 5,484,437 A | 1/1996 | Michelson | |
| 5,554,101 A | 9/1996 | Matula et al. | |
| 5,569,205 A | 10/1996 | Hart et al. | |
| 5,746,763 A | 5/1998 | Benderev et al. | |
| 5,762,629 A | 6/1998 | Kambin | |
| 5,792,044 A * | 8/1998 | Foley et al. | .................. 600/114 |
| 5,797,909 A | 8/1998 | Michelson | |
| 5,868,758 A * | 2/1999 | Markman | ..................... 606/133 |
| 5,976,146 A | 11/1999 | Ogawa et al. | |
| 6,004,326 A | 12/1999 | Castro et al. | |
| 6,152,871 A | 11/2000 | Foley et al. | |
| 6,228,022 B1 | 5/2001 | Friesem et al. | |
| 6,296,647 B1 | 10/2001 | Robioneck et al. | |

(Continued)

FOREIGN PATENT DOCUMENTS

WO    WO 97/23174    7/1997

(Continued)

OTHER PUBLICATIONS

METRX System MicroEndoscopic Discectomy—Maurice M. Smith, M.D., Kevin T. Foley, M.D., 1999 Sofamor Danek, pp. 1-22.

(Continued)

*Primary Examiner*—Pedro Philogene

(57) ABSTRACT

Access to a greater area of surgical site with minimally invasive procedure is obtained by using two sets of sequentially placed tissue dilators oriented with their axes in a plane parallel to the spinal axis and a final non-circular dilator encompassing the two sets, followed by a non-circular tubular retractor providing a working channel extending longitudinally of the spine.

20 Claims, 7 Drawing Sheets

U.S. PATENT DOCUMENTS

| | | | |
|---|---|---|---|
| 6,383,191 B1 | 5/2002 | Zdeblick et al. | |
| 6,551,270 B1 | 4/2003 | Bimbo et al. | |
| 6,575,981 B1 * | 6/2003 | Boyd et al. | 606/90 |
| 6,648,895 B2 | 11/2003 | Burkus et al. | |
| 6,916,330 B2 * | 7/2005 | Simonson | 606/191 |
| 2001/0016741 A1 | 8/2001 | Burkus et al. | |
| 2003/0083688 A1 | 5/2003 | Simonson | |

FOREIGN PATENT DOCUMENTS

| | | |
|---|---|---|
| WO | WO 99/52453 | 10/1999 |
| WO | WO 02/062235 | 8/2002 |

OTHER PUBLICATIONS

METRX Microdiscectomy Surgical Technique—Donald L. Hilton, Jr., Sylvain Palmer, 2001 Sofamor Danek, pp. 1-18.

* cited by examiner

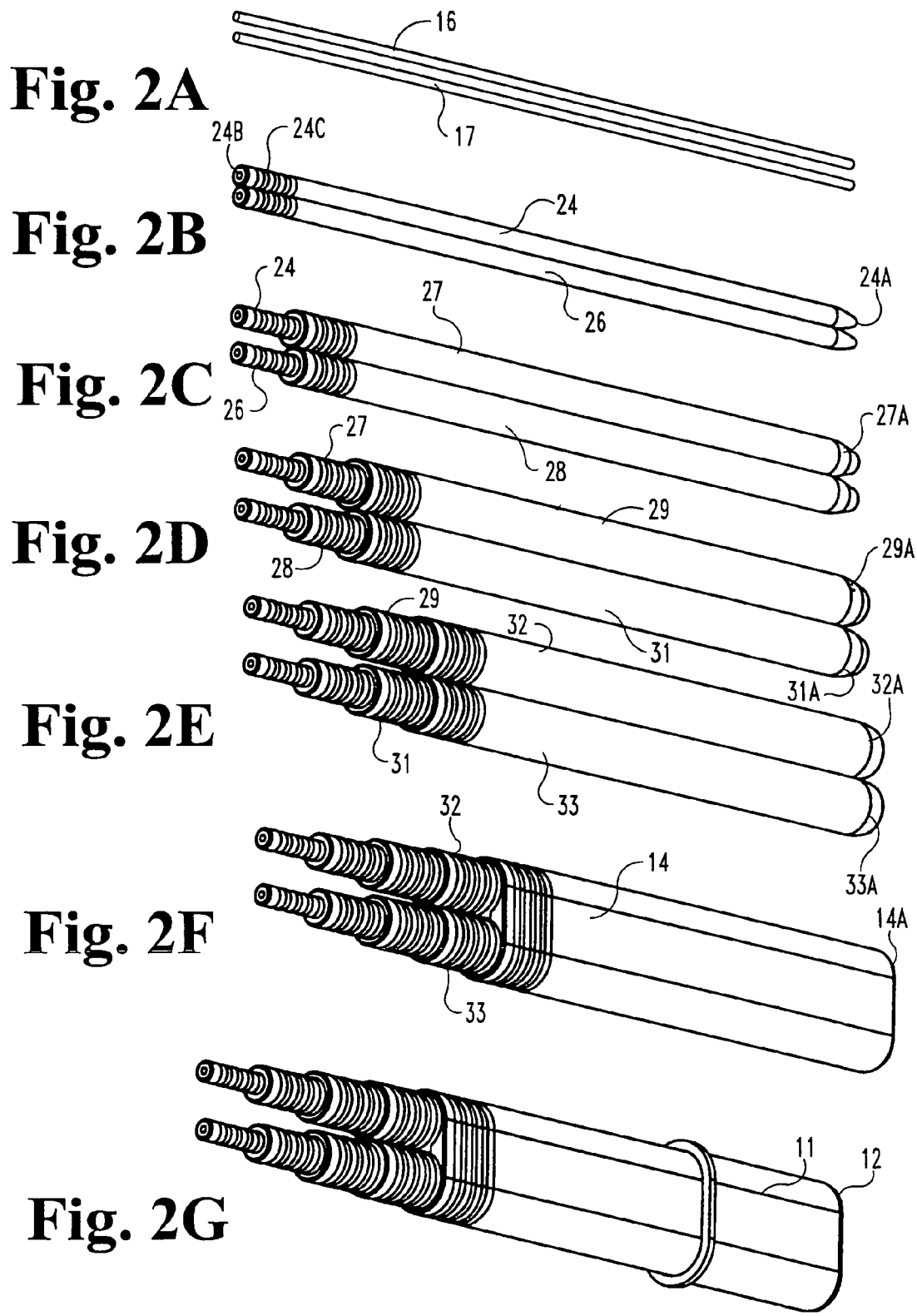

OVAL DILATOR AND RETRACTOR SET AND METHOD

CROSS-REFERENCE TO RELATED APPLICATION

This application is a divisional of U.S. patent application Ser. No. 10/246,995 filed on Sep. 19, 2002, and issued as U.S. Pat. No. 7,074,226, which is incorporated herein by reference.

BACKGROUND

The present invention relates to instruments and methods for performing tissue retraction for surgeries using minimally invasive procedures.

Traditional surgical procedures for pathologies located within the body can cause significant trauma to the intervening tissues. These procedures often require a long incision, extensive muscle stripping, prolonged retraction of tissues, denervation and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

U.S. Pat. No. 5,792,044 issued to Kevin T. Foley et al. provides rather extensive background information pertaining to percutaneous surgery. FIGS. 10a through 10i of that patent depict, and column 10 at lines 11 and following of the patent describe, steps of a method for access to a surgical site in the spine. As described, it begins with the insertion of a guide wire followed by a series of successfully larger dilators installed in sequence to dilate the soft tissues. Then, following installation of the largest dilator deemed necessary, a cannula (retractor) is advanced over the largest dilator for providing a working channel from the skin of the patient to working space adjacent the spine. The retractor can be secured in place by any of the many suitable means known in the art, several of which are mentioned in the patent. It is desirable to be able to use the working channel provided by the retractor, for surgical tools, for viewing devices and for inserting and manipulating fixation elements to the maximum extent possible for desired placement and fixation. Some such items or combinations of items dictate the inside diameter needed in the retractor.

It is sometimes desirable to have working space at the spine extending a greater distance axially of the spine than transversely. However, to provide such access through the typical circular retractors using the above-mentioned dilation techniques, could require a diameter so great as to cause significant trauma to the intervening tissues during placement of the dilators and the tubular retractor.

The development of minimally invasive percutaneous procedures has yielded a major improvement in reducing recovery time and post-operative pain because minimal dissection of tissue (such as muscle tissue, for example) is required. Minimally invasive surgical techniques are desirable for spinal and neurosurgical applications because of the need for access to locations within the body, and the danger of damage to vital intervening tissues. While developments in minimally invasive surgery are steps in the right direction, there remains a need for further development in minimally invasive surgical instruments and methods.

SUMMARY

One aspect of the present invention is providing a minimally invasive but an optimally oriented working channel for access to spinal surgery sites at the spine.

Another aspect is providing an improved shape of working channel.

Another aspect is providing a way to access greater working space adjacent the spine with minimal trauma to tissue between the skin and the spine.

BRIEF DESCRIPTION OF THE DRAWINGS

FIG. 2A-2G depict the series of steps and associated dilator tubes employed according to a method of the present invention.

DESCRIPTION OF THE ILLUSTRATED EMBODIMENT

Figure 1A:
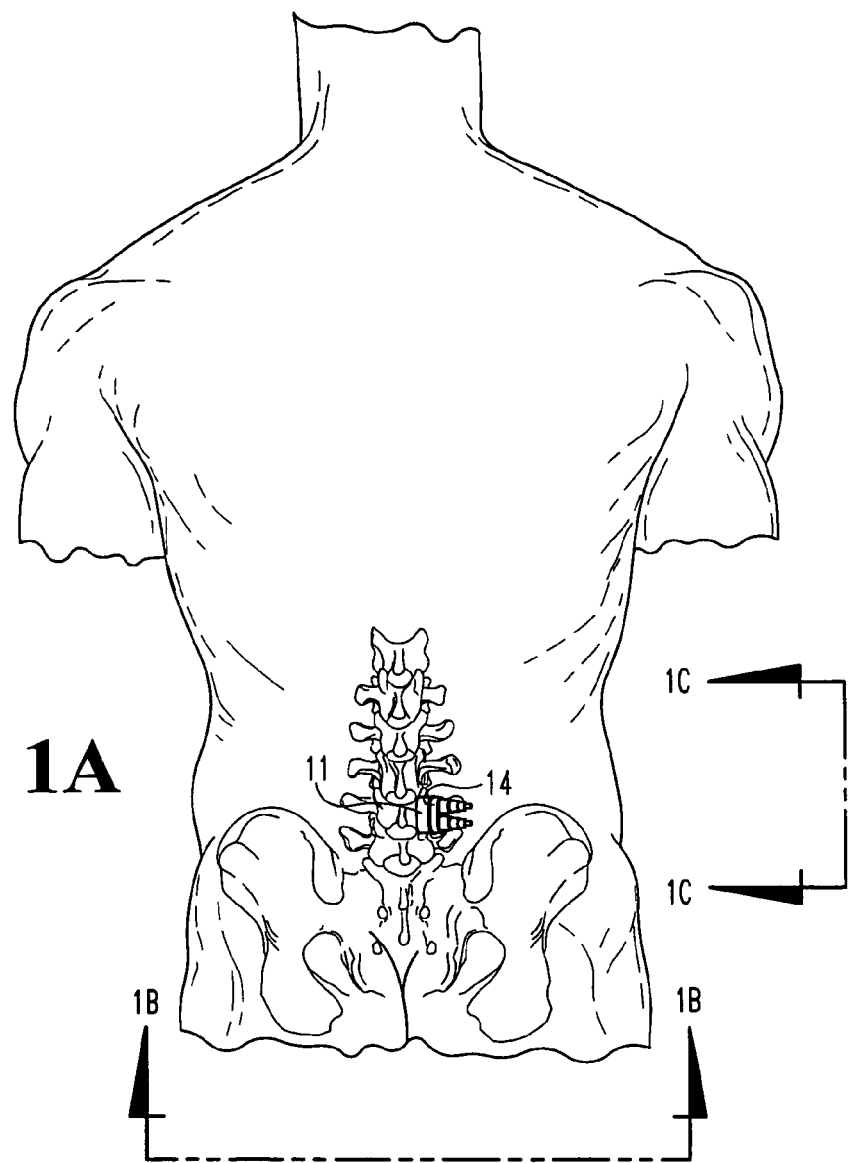
FIG. 1A is a schematic drawing of a portion of the spine viewed in the back to front direction and showing an oval dilator and an oval tubular retractor according to one embodiment of the present invention, and placed at a planned surgical site, according to a method of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1B:
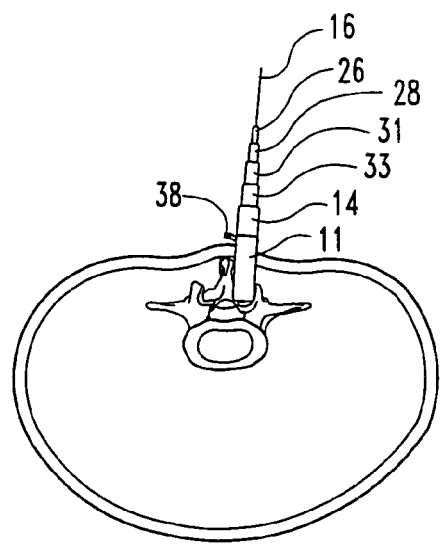
FIG. 1B is a schematic view along a line in a direction of arrows B-B in FIG. 1A.
Figure 1C:
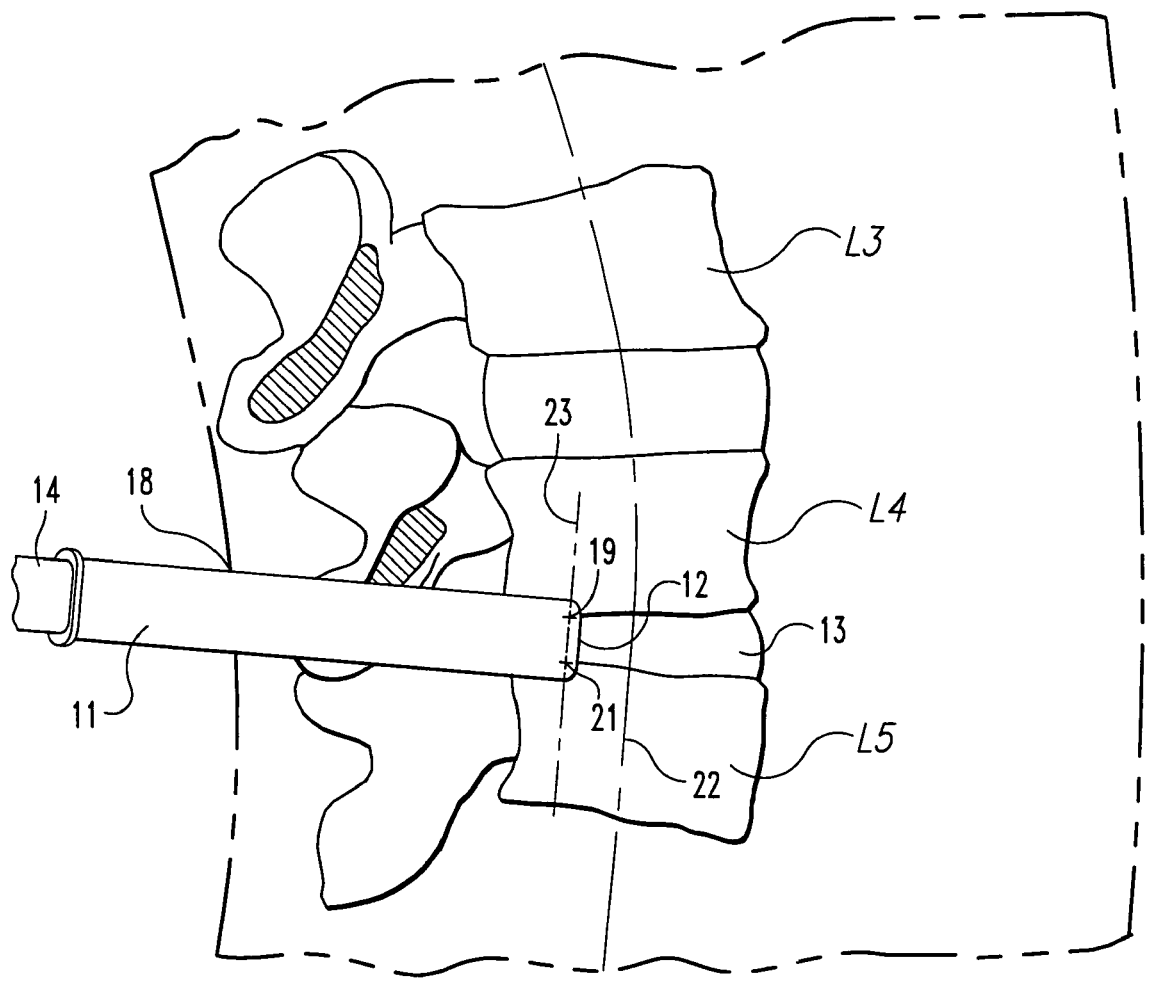
FIG. 1C is a schematic view in the direction of arrows C-C in FIG. 1A.

With reference to FIGS. 1A-1C, lumbar vertebrae L3, L4 and L5 are illustrated schematically with the planned surgical site being at the L4-L5 joint through a posterion approach. The tubular retractor 11 according to the illustrated embodiment of the present invention is shown in place with its distal end 12 contacting the laminae of L4 and L5 at the site where the intervertebral disc 13 will be addressed. The oval dilator 14 is shown receiving the retractor 11. Tubular retractor 11 and oval dilator 14 can also be positioned at other locations along the spine and in other approaches to the spine, including lateral, postero-lateral, antero-lateral and anterior approaches.

Current tissue dilation practice with a single guide wire and a sequence of dilators positioned over the single guide wire is shown and described in a publication entitled *METRx Microdiscectomy Surgical Technique*, published in 2001 by Medtronic Sofamor Danek of Memphis, Tenn., USA, the entire contents of which publication are incorporated herein by reference. The METRx™ System for microdiscectomy, marketed by Medtronic Sofamor Danek, USA of Memphis, Tenn., includes a set of circular dilator tubes in diameters from 5.3 mm to 16.8 mm that are positioned one over the other to receive a circular retractor of desired size.

The present invention can be practiced with or without guide wires. An example of the present invention with guide wires will be described first. So, referring now to FIGS. 2A through 2G, FIG. 2A shows a couple of guide wires 16 and 17 which are vertically spaced. Using conventional visualization technique, these wires are inserted through an incision in the skin at 18 and advanced through tissue to spinal bone at points 19 and 21, for wires 16 and 17, respectively, on the vertebrae. If desired, they can be advanced forcefully enough to become anchored at an appropriate spacing in a bony face or faces, depending upon the specific site to which the surgery is addressed. It is further contemplated that guide wires 16 and 17 could be anchored to bone and/or tissue at other locations of the posterior spine and in locations to accommodate other approached to the spine.

At a spinal surgery site, the spine has an axis in a direction from head toward feet which may be referred to hereinafter as a primary axis. At the site illustrated herein, the primary axis is designated by the line 22. According to one feature of the invention, the cross-sectional shape of the tubular retractor 11 is non-circular, and has a generally elliptical or oval shape having a major axis parallel to the axis 22 of the spine. Accordingly, the wire-to-bone contact points (or anchor points, if desired) are on an axis or line 23 parallel to axis 22 of the spine at the surgery site. By orienting the major axis parallel to or in the general direction of axis 22, access can be provided to multiple vertebral elements through a single working channel. For example, in FIG. 1C, access to each of the vertebrae L4 and L5 can be provided through the working channel of oval tubular retractor 11 to accommodate procedures and/or implant-insertion into each of the vertebrae L4 and L5 with little or no repositioning of the distal end of oval tubular retractor 11.

Following installation of the guide wires, the first pair of dilators 24 and 26 is installed on the wires 16 and 17, respectively. Each of the dilators is a circular tube with a central aperture throughout its length and sized to enable sliding the dilator along the length of the guide wire until the rounded distal end for tube 24, for example, engages a bony face or other tissue at point 19 or tissue adjacent the surgical site. A series of grooves 24G is provided in each tube near the proximal end such as 24P, the series extending from adjacent the proximal end toward the distal end a short distance, to facilitate grasping the tube during insertion and later when removed from the body.

Following insertion of the dilators 24 and 26, and the distal ends against the bone or other tissue, larger dilators 27 and 28 are placed on the dilators 24 and 26, respectively, and advanced along them until abutment of their distal ends, such as 27A for dilator 27, with bone or other tissue adjacent the surgical site. These dilators are similar to dilators 24 and 26 except for the larger size and shorter length.

Then dilators 29 and 31 are placed over and advanced along dilators 27 and 28, respectively, until the distal ends 29A and 31A of these dilators contact the bone or other tissue adjacent the surgical site.

Then dilators 32 and 33 are installed and advanced over the dilators 29 and 31, respectively, and advanced along until their distal ends 32A and 33A contact the bone or other tissue adjacent the surgical site.

As each of the aforementioned dilators (which may be referred to as "precursor dilators") is placed, the soft tissue is dilated with minimal trauma. Also, the set of dilators is oriented such that a plane containing the longitudinal axes of all of them, also contains the line 23 which is parallel to the spinal axis 22 and may, in some instances, be co-planar with the spinal axis 22, depending upon the direction of access desired by the surgeon.

After insertion of the last set of the circular precursor dilators, oval dilator 14, according to the illustrated embodiment of the invention, is installed. It is advanced over the dilators 32 and 33 until the distal end 14A thereof is located where the surgeon desires, which can be in contact with the laminae of at least one of the vertebrae or adjacent other paraspinous tissue and/or other portions of the vertebral bodies. Following the seating of the oval dilator 14, the oval tubular retractor 11 according to the invention is advanced along the oval dilator 14 until its distal end 12 contacts or is proximate bone or paraspinous tissue at the surgery site.

Following positioning of the oval tubular retractor 11, the precursor dilators, and guide wires if not already removed, can be removed in any desired sequence or as a group, depending upon the convenience of the surgeon. The staggered lengths and gripping surfaces near the proximal ends thereof facilitate this. Once these dilators and oval dilator 14 have been removed, the oval tubular retractor 11 remains in place, providing a working channel through which viewing devices, instruments, fixation devices and materials may be passed. Some examples of the type of viewing systems that can be used with the tubular retractor of the present invention are those that are available with the above-mentioned METRx System, which includes microscopic viewing systems positioned over the proximal end of the retractor, and endoscopic viewing systems positioned through the retractor. Tubular retractor 11 could also be used with other viewing systems, such as those that include an endoscope positioned to the surgical site through a second portal and/or fluoroscopic viewing systems.

Figure 3:
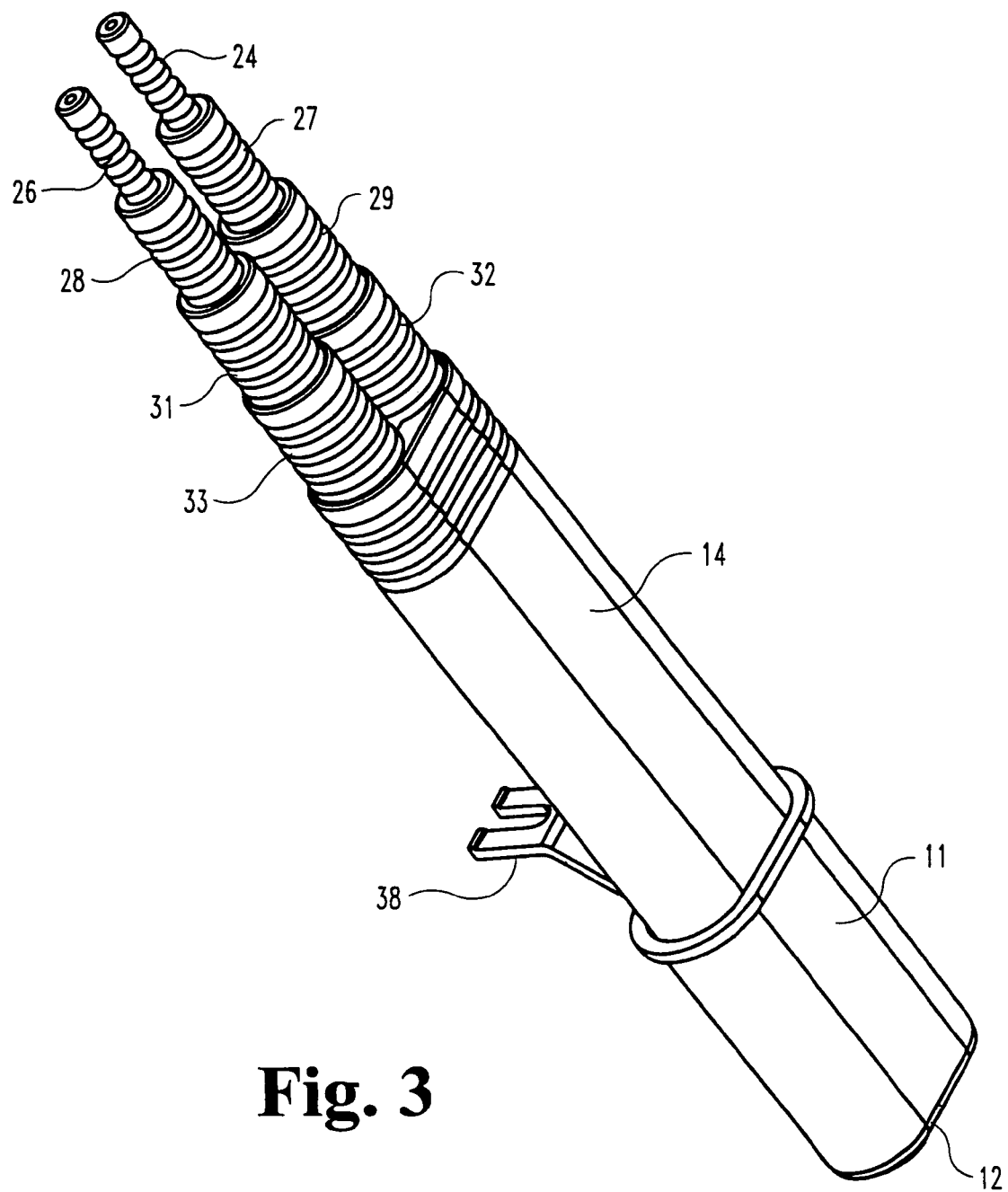
FIG. 3 is an enlarged view similar to FIG. 2G and showing a mounting bracket on the tubular retractor associated with the set of dilators.
Figure 4:
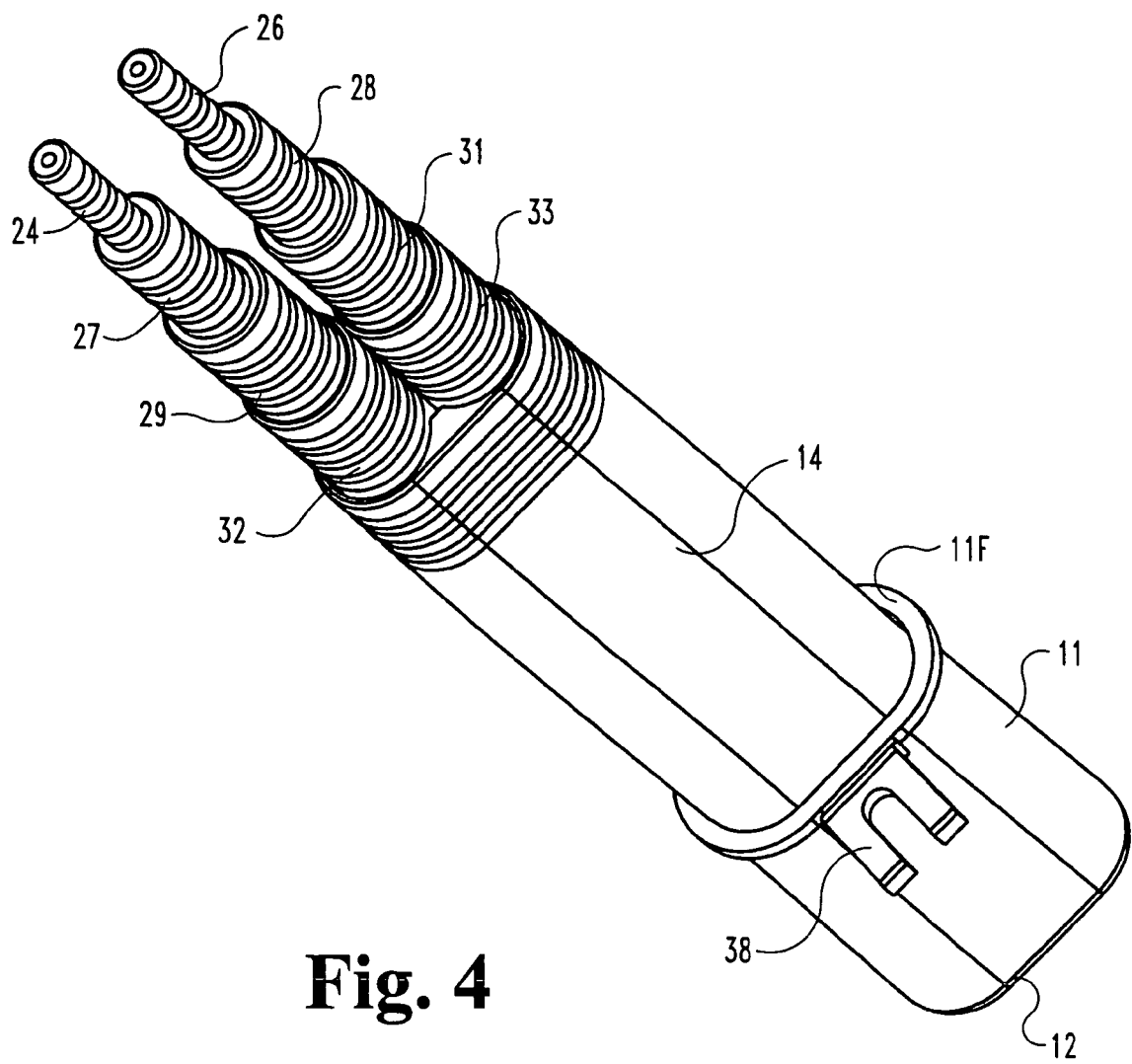
FIG. 4 is a view of the combination of dilators of FIG. 3 but showing them at a different angle.

Referring now to FIG. 3, the combination shown is much like that of FIG. 2G, but a mounting bracket 38 is shown on the oval tubular retractor 11. The mounting bracket can be secured to a flexible arm or other device mounted to the surgical table or other fixture in the operating room.

Figure 5:
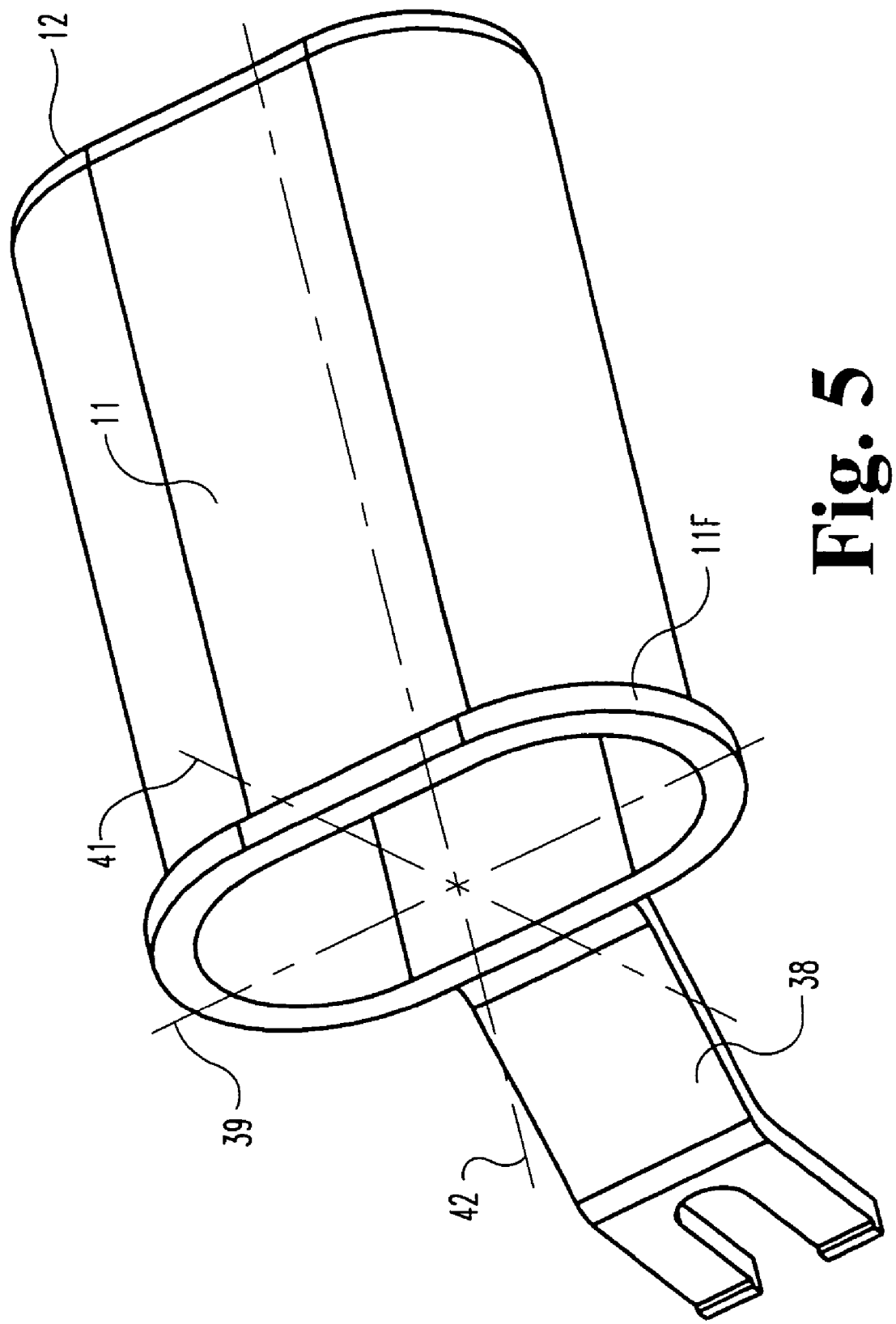
FIG. 5 is a view of the tubular retractor itself.

FIG. 5 shows the tubular retractor 11 and bracket 38 and the oval internal shape of the tube and which becomes the working channel in the patient's body. In this illustrated embodiment, the tube cross section is somewhat elongate with relatively straight sides and round ends. Accordingly this oval has a major axis 39, and a minor axis 41 perpendicular to the major axis. When this retractor is in place at the surgery site, the axis 39 is in the same plane as line 23 (FIG. 1).

While the longitudinal axis 42 of the oval tubular retractor is intended to bisect a line between points 19 and 21 in the vertebrae, and the axis 39 lies in a plane containing the longitudinal axis 42 and parallel to a plane containing the primary spinal axis 22 at the site of the surgery, it is conceivable that the axis 39 will not be perfectly parallel to axis 22. This would be the case if it is found preferable to tip the axis 42 slightly in a vertical plane to avoid interference with and the necessity for removal of some bony structure or tissue material for access to the surgical site. It may also be desired to reposition the distal end 12 of oval retractor 11 from its initial insertion position over paraspinous tissue located outside the location of the working channel of oval retractor 11 by manipulating oval retractor 11 through the skin and tissue of the patient.

Figures 6, 7:
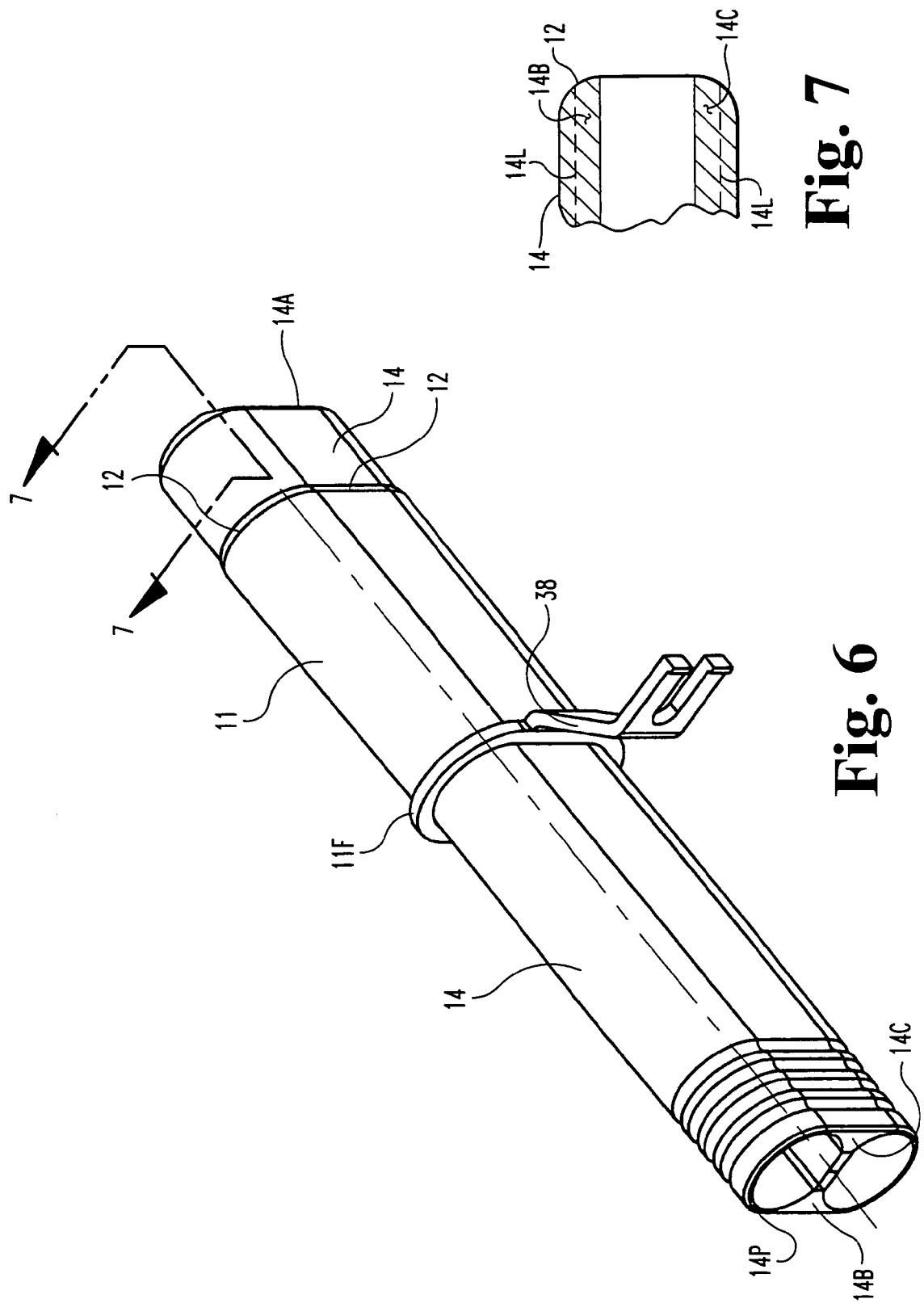
FIG. 6 is a view of the tubular retractor with the oval dilator received through it but without the smaller round dilators.
FIG. 7 is a longitudinal section of a fragment of the oval dilator taken at line 7-7 in FIG. 6 and viewed in the direction of the arrows.

Referring now the FIG. 6, the oval dilator 14 is shown with the oval retractor 11 slid partway between the distal end 14A and proximal end 14P of the oval dilator. Since the pair of circular cross-section dilators 32 and 33 present a grooved contour or valley at their junction and along their entire length, a volume of tissue along each side of the pair might not be entirely dilated at the time for installation of the oval dilator 14. Therefore, the oval dilator is provided with a pair of longitudinally extending internally projecting ribs 14B and 14C as shown in FIG. 6 and extending from the proximal end 14P to the distal end 14A. To facilitate dilation of the above mentioned volume of tissue as the oval dilator is inserted, the leading internal edge of each of the ribs 14B and 14C is curved, as is the contour of the entire leading edge of the oval dilator 14, as shown in FIG. 7.

The thickness of the tube wall section at the ribs 14B and 14C relative to the wall thickness at the top and bottom of the oval dilator is indicated by the dashed lines 14L in FIG. 7. Ribs 14B and 14C can extend into the channel of dilator 14, and facilitate alignment of oval dilator 14 along the pair of adjacent circular cross-section dilators 32 and 33.

The externally projecting perimetrical flange 11F on the oval retractor provides a useful feature on which the bracket 38 or some other sort of bracket, if desired, can be incorporated at the point of manufacture of the retractor. Viewing instruments and/or other surgical instruments can be mounted to the oval retractor 11 on flange 11*f*.

The invention can be practiced without guide wires, if desired. Following an incision, the first dilator tube is inserted and guided using fluoroscopy or other visualization technique until its distal end contacts vertebral bone or other tissue at the desired location. Then, through the same incision, the second dilator tube is inserted, side-by-side with the first and advanced to contact of its distal end with the bone. Then a third dilator is installed on the first dilator and advanced to contact its distal end with the bone. Then a fourth dilator is installed on the second dilator and advanced to contact of its distal end with the bone. This process continues in the same manner as described above until the dilation is sufficient to accommodate the size of oval tubular retractor to be used. As each set of dilators is inserted, it can contact the wall of the adjacent dilator and provide an additional separation between the side-by-side dilators that corresponds to about one-half of the increase in the external diameter of the dilator being inserted over the external diameter of the dilator receiving the inserted dilator.

The materials used in the guide wires, dilators and retractor can be stainless steel, aluminum, plastic, or any other material suitable for surgical instruments. The amterial can be opaque, translucent or combinations thereof. Specific examples of circular dilator tube diameters useful with the present invention and found in the above-mentioned publication are: 5.3 mm, 9.4 mm, 12.8 mm, 14.6 mm, and 16.8 mm, and one specific example guide wire diameter is 0.062 inch. Other dilator and guide wire diameters are also contemplated.

One example of dimensions of the major and minor axes of the oval tubular dilator 14 of the present invention may be 40 mm and 20 mm, respectively. A smaller one may be 28 mm and 14 mm, respectively. Other sizes may be provided if desired. Oval tubular retractor 11 would have internal dimensions so that they slidably fit the oval dilators which slidably fit the round dilators as described above. Examples of lengths may be 3 cm to 9 cm. The length chosen will usually be the shortest that provides access to the surgical site or working space adjacent the spine, such as, for example, the vertebra lamina while allowing maximum mobility of instruments in the working channel. The oval retractors 11 can be provided in a set or kit of oval retractors 11 having various lengths from which the surgeon can select.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A dilator combination used in soft tissue of an animal body to provide access to a planned surgical site adjacent the spine and comprising:
   a first set of telescoped tissue-dilator tubes coaxial with a first axis;
   a second set of telescoped tissue-dilator tubes coaxial with a second axis, wherein said second set of telescoped tissue-dilator tubes is located in side-by-side relation to said first set of telescoped tissue dilator tubes; and
   an enveloping dilator tube having a proximal end and a distal end and a non-circular cross-section, said enveloping dilator tube encompassing said first and second sets of dilator tubes in said side-by-side relation and slidably received on said first and second sets.

2. The combination of claim 1 and wherein:
   said second set of telescoped tissue-dilator tubes are in contact with said first set of said telescoped tissue dilator tube in said side-by-side relation.

3. The combination of claim 2 and wherein:
   said non-circular cross-section has a shape in a plane perpendicular to said first axis;
   said shape is the same from said first location to said second location; and
   said shape has a major axis and a minor axis.

4. The combination of claim 3 and wherein:
   the overall dimension of said enveloping dilator along said major axis is between 28 and 40 mm; and
   the overall dimension of said enveloping dilator along said minor axis is between 14 and 20 mm.

5. The combination of claim 3 and wherein:
   said shape is elongate with parallel sides and circular ends with radii, the radii centers of the ends being on a line bisecting the minor axis.

6. The combination of claim 1 and wherein:
   said enveloping dilator tube has perimetrical external ribs longitudinally spaced in a series extending from said proximal end toward, said distal end.

7. The combination of claim 1, wherein said enveloping dilator tube includes a channel extending along a longitudinal axis and said channel includes a non-circular cross-sectional shape in a plane perpendicular to said longitudinal axis at a first location proximate said distal end, said enveloping dilator tube further including an external surface having a cross-sectional shape at said first location, wherein said cross-sectional shape of said channel differs from said cross-sectional shape of said external surface.

8. The combination of claim 7, wherein said external surface includes parallel sides and circular, ends extending between said parallel sides at least adjacent said distal end of said tube and wherein said cross-sectional shapes of said channel and said external surface extend from said first location proximate said distal end to a second location at least eighty percent of the distance from said distal end to said proximal end.

9. The combination of claim 1, wherein said non-circular cross-section includes an external surface of said enveloping dilator tube that forms an oval shape in said cross-section and said non-circular cross-section extends from a first location proximate said distal end to a second location at least eighty percent of the distance from said distal end to said proximal end.

10. The combination of claim 1, wherein said enveloping dilator tube includes a channel and said first and second sets of telescoped tissue-dilator tubes are positioned in said channel and each include a circular cross-section perpendicular to said first and second axes.

11. The combination of claim 1, further comprising a retractor having a working channel sized and shaped to receive said enveloping dilator tube in said working channel, said working channel of said retractor including a cross-sectional shape corresponding to a cross-sectional shape of an external surface of said enveloping dilator tube.

12. The combination of claim 1, wherein said first and second set of telescoped tissue dilator tubes are received in a channel of said enveloping tissue dilator at a location offset from a central axis of said enveloping dilator tube.

13. The combination of claim 1, wherein said enveloping dilator tube is open and said distal and proximal ends thereof and said first and second sets of telescoped tissue-dilator tubes extend proximally from said proximal end.

14. A dilator combination used in soft tissue of an animal body to provide access to a planned surgical site adjacent the spine and comprising:
- at least one first dilator tube extending along a first axis and having a circular cross-section transversely to said first axis;
- at least one second dilator tube extending along a second axis and having a circular cross-section transversely to said second axis, said at least one second dilator tube in side-by-side relation to and in contact with said at least one first dilator tube; and
- an enveloping dilator tube having a proximal end and a distal end and a channel extending along a longitudinal axis and said channel including a non-circular cross-sectional shape transversely to said longitudinal axis, said enveloping dilator tube encompassing said first and second dilator tubes in said channel with said first and second dilator tubes in side-by-side relation to one another.

15. The combination of claim 14, wherein said enveloping dilator includes an external surface having a non-circular cross-sectional shape transversely to said longitudinal axis.

16. The combination of claim 15, wherein said cross-sectional shape of said external surface is different than said cross-sectional shape of said channel.

17. The combination of claim 16, wherein said cross-sectional shape of said external surface is oval.

18. The combination of claim 17, wherein said enveloping dilator tube has perimetrical external ribs longitudinally spaced in a series extending from said proximal end toward said distal end.

19. A dilator combination used in soft tissue of an animal body to provide access to a planned surgical site adjacent the spine and comprising:
- at least one first set of dilator tubes coaxial with a first axis and having a circular cross-section transversely to said first axis;
- at least one second set of dilator tubes coaxial with a second axis and having a circular cross-section transversely to said second axis, wherein said at least one second set of dilator tubes is in side-by-side relation to and in contact with said at least one first set of dilator tubes; and
- an enveloping dilator tube having a proximal end and a distal end, said enveloping dilator tube including a channel and an external surface extending along a longitudinal axis between said proximal and distal ends, said channel and said external surface each including a non-circular cross-sectional shape transversely to said longitudinal axis, said enveloping dilator tube encompassing said first and second sets of dilator tubes in said channel with said first and second sets of dilator tubes in side-by-side relation to one another.

20. The combination of claim 19, wherein said non-circular cross-sectional shapes of said channel and said external surface are different from one another.

* * * * *

UNITED STATES PATENT AND TRADEMARK OFFICE
CERTIFICATE OF CORRECTION

PATENT NO.       : 7,618,431 B2
APPLICATION NO. : 11/478041
DATED            : November 17, 2009
INVENTOR(S)      : Roehm, III et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 338 days.

Signed and Sealed this

Twenty-sixth Day of October, 2010

David J. Kappos
*Director of the United States Patent and Trademark Office*